(12) United States Patent
Chappo et al.

(10) Patent No.: US 8,525,122 B2
(45) Date of Patent: Sep. 3, 2013

(54) DATA ACQUISITION

(75) Inventors: Marc Chappo, Elyria, OH (US); Randall P. Luhta, Highland Heights, OH (US); Christopher J. Vrettos, Willoughby, OH (US); Brian E. Harwood, Rocky River, OH (US)

(73) Assignee: Koninklijke Philips N.V., Eindhoven (NL)

( * ) Notice: Subject to any disclaimer, the term of this patent is extended or adjusted under 35 U.S.C. 154(b) by 174 days.

(21) Appl. No.: 13/254,173

(22) PCT Filed: Feb. 18, 2010

(86) PCT No.: PCT/IB2010/050723
§ 371 (c)(1),
(2), (4) Date: Sep. 1, 2011

(87) PCT Pub. No.: WO2010/109353
PCT Pub. Date: Sep. 30, 2010

(65) Prior Publication Data
US 2012/0001076 A1    Jan. 5, 2012

Related U.S. Application Data

(60) Provisional application No. 61/163,493, filed on Mar. 26, 2009.

(51) Int. Cl.
*G01T 1/20*    (2006.01)
(52) U.S. Cl.
USPC .................................................. 250/370.11
(58) Field of Classification Search
USPC .................................................. 250/370.11
See application file for complete search history.

(56) References Cited

U.S. PATENT DOCUMENTS

| 4,052,620 A | 10/1977 | Brunnett |
| 4,068,306 A | 1/1978 | Chen et al. |
| 5,103,092 A | 4/1992 | Takahashi et al. |
| 6,407,390 B1 * | 6/2002 | Rozsa ...................... 250/363.01 |

(Continued)

FOREIGN PATENT DOCUMENTS

| EP | 1091216 A1 | 4/2001 |
| EP | 1139119 A2 | 10/2001 |
| WO | 2007141388 A1 | 12/2007 |

OTHER PUBLICATIONS

Luhta, R., et al.; A new 2D-tiled detector for multislice CT; 2006; Medical Imaging; vol. 6142; pp. 275-286.

*Primary Examiner* — David Porta
*Assistant Examiner* — Hugh H Maupin

(57) ABSTRACT

An imaging detector includes processing electronics (208) with a thermal coefficient about equal to a negative of a summation of thermal coefficients of a photosensor array (204) and a scintillator array (202) of the detector. In another instance, the imaging detector includes an A/D converter (302) that alternately converts first charge corresponding to impinging radiation into a first signal and second charge corresponding to decaying charge into a second signal and a logic unit (308) that corrects the first signal based on the second signal. In another instance, the imaging detector includes an A/D converter (302), an integrator offset voltage signal determiner (318), and a logic unit (308), wherein the determiner (318) induces an electrical current via an offset voltage, the A/D converter (302) measures the current, and the logic unit (308) calculates a resistance of the photosensor array (204) based on the reference voltage and the measured current.

15 Claims, 7 Drawing Sheets

(56) References Cited

U.S. PATENT DOCUMENTS

| | | |
|---|---|---|
| 6,510,195 B1 | 1/2003 | Chappo et al. |
| 6,671,345 B2 | 12/2003 | Vrettos et al. |
| 7,113,563 B2 | 9/2006 | Kamimura et al. |
| 7,489,883 B2 | 2/2009 | Rossi et al. |
| 7,822,173 B2 | 10/2010 | Mattson et al. |
| 2002/0070343 A1* | 6/2002 | Hoffman ................ 250/367 |
| 2009/0121146 A1 | 5/2009 | Luhta et al. |

* cited by examiner

DATA ACQUISITION

CROSS REFERENCE TO RELATED APPLICATIONS

This application claims the benefit of U.S. provisional application Ser. No. 61/163,493 filed Mar. 26, 2009, which is incorporated herein by reference.

The following generally relates to data acquisition, and finds particular application to computed tomography (CT). However, it also amenable to other medical imaging applications and to non-medical imaging applications.

A computed tomography (CT) scanner includes an x-ray tube mounted on a rotatable gantry that rotates around an examination region about a longitudinal or z-axis. A detector array subtends an angular arc opposite the examination region from the x-ray tube. The detector array detects radiation that traverses the examination region. The detector array includes a scintillator array optically coupled to a photosensor array, which is electrically coupled to processing electronics. For each data acquisition integration period, the scintillator array generates light indicative of radiation impinging thereon, the photosensor array generates an electrical signal indicative of the light, and the processing electronics generates digital data indicative of the detected radiation based on the electrical signal. A reconstructor reconstructs the digital data and generates volumetric image data, which can be processed to generate one or more images.

Unfortunately, the scintillator array and the photosensor array have non-zero and different thermal coefficients. As such, the response of the scintillator array and the photosensor array may vary with temperature. As a consequence, artifacts such as ring artifact may be introduced into the image data. One trend has been to employ stringent temperature control for the detector array. In one instance, this includes maintaining the detector array within a predetermined temperature range using heaters, fans, heat sinks, etc. However, such temperature control can be costly, and imaging performance can still be compromised if the temperature control is not adequate. Another factor that can add cost is a lack of ability to test photosensor channels prior assembling the detector array and exposing the detector array to x-ray and/or light.

Furthermore, the charge deposited on a scintillator crystal by an impinging photon decays with a relatively long time constant (e.g., on the order of seconds), which is referred to as afterglow. As a consequence, residual charge from a photon impinging on the scintillator crystal in a first integration period may add to the charge deposited by a photon impinging the scintillator crystal in a subsequent integration period. This residual charge is often referred to as dark current and is integrated along with the charge from the photon in the next subsequent period, which may compromise imaging performance. A trend has been to use a scintillation material with low afterglow. However, scintillators with lower afterglow generally are more expensive and less efficient than scintillators with higher afterglow.

Aspects of the present application address the above-referenced matters and others.

According to one aspect, an imaging system includes a photosensor array having a light sensitive side and an opposing read out side. A scintillator array is optically coupled to the light sensitive side of the photosensor array, and processing electronics are electrically coupled to the read out side of the photosensor array. The photosensor array, the scintillator array, and the processing electronics are in thermal communication, and a value of a thermal coefficient of the processing electronics is about equal to a negative of a summation of a thermal coefficient of the photosensor array and a thermal coefficient of the scintillator array.

In another embodiment, an imaging detector includes a photosensor array, a scintillator array optically coupled to the photosensor array, and processing electronics electrically coupled to the photosensor array. The processing electronics includes an A/D converter that converts charge output by the photosensor array into a digital signal having a frequency indicative of the charge. The A/D converter alternately converts first charge corresponding to impinging radiation into a first signal and second charge corresponding to decaying charge into a second signal. A logic unit corrects the first signal based on the second signal.

In another embodiment, an imaging detector includes a photosensor array, a scintillator array optically coupled to the photosensor array, and processing electronics electrically coupled to the photosensor array. The processing electronics includes an A/D that converts charge output by the photosensor array into a digital signal having a frequency indicative of the charge, and an integrator offset voltage signal setter that sets an integrator offset voltage signal for the A/D converter that induces an electrical current measurable by the A/D converter.

In another embodiment, an imaging system includes a radiation source that generates a radiation beam that traverses an examination region a detector array that detects radiation that traverses the examination region, and a reconstructor that reconstructs the output of the detector array and generates imaged data indicative thereof. The detector array includes a plurality of detector tiles, and a detector tile includes a photosensor array, a scintillator array optically coupled to the photosensor array, and processing electronics electrically coupled to the photosensor array. The photosensor array, the scintillator array and the processing electronics are in thermal communication, and a value of a thermal coefficient of the processing electronics is about equal to a summation of a thermal coefficient of the photosensor array and a thermal coefficient of the scintillator array.

In another embodiment, a method includes setting a value of a thermal coefficient of processing electronics of a detector tile of an imaging system about equal to a summation of thermal coefficients of a photosensor array and a scintillator array of the detector tile.

In another embodiment, a method includes pulsing radiation emission on and off during at least on integration period during an imaging procedure, detecting a first signal during the at least one integration period when radiation emission is on, detecting a second signal during the at least one integration period only when radiation emission is off, and correcting the first signal based on the second signal.

In another embodiment, a method includes injecting a signal into an input of an A/D converter of a detector tile, wherein the signal is measurable by the A/D converter, converting the signal into digital data with the A/D converter, and computing a resistance of a photosensor array of the detector tile based on the injected signal and the digital data.

The invention may take form in various components and arrangements of components, and in various steps and arrangements of steps. The drawings are only for purposes of illustrating the preferred embodiments and are not to be construed as limiting the invention.

Figure 1:
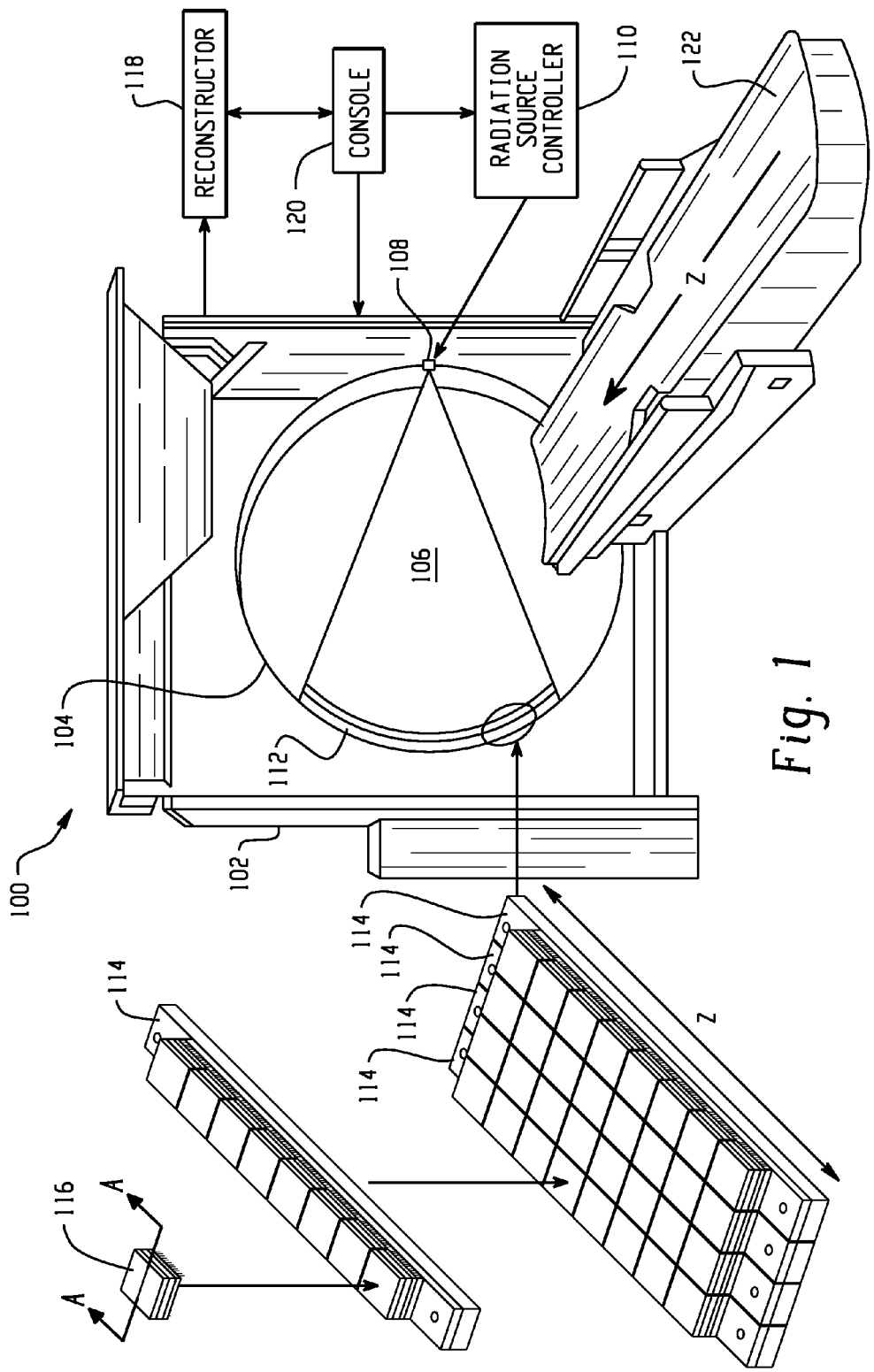
FIG. 1 illustrates an example imaging system.

FIG. 1 illustrates an imaging system 100 such as a computed tomography (CT) scanner. The imaging system 100 includes a generally stationary gantry 102 and a rotating gantry 104. The rotating gantry 104 is rotatably supported by the stationary gantry 102 and rotates around an examination region 106 about a longitudinal or z-axis.

A radiation source 108 such as an x-ray tube is supported by the rotating gantry 104 and emits radiation that traverses the examination region 106. A radiation source controller 110 controls the radiation source 108. Such control includes, but is not limited to, turning the radiation source 108 on and off and, hence, turning radiation emission on and off. This can be achieved through grid switching and/or otherwise. In one instance, the radiation source 108 is pulsed during an integration period so that radiation is on for a first sub-portion of the integration period and off for a second sub-portion of the integration period. As described in greater detail below, the dark current from scintillator afterglow can be measured when radiation is off, and the measurement can subsequently be used to correct the signal corresponding to the detected radiation.

A radiation sensitive detector array 112 subtends an angular arc opposite the radiation sources 108 across the examination region 106 and detects radiation traversing the examination region 106. In the illustrated embodiment, the radiation sensitive detector array 112 includes a plurality of detector modules 114 arranged with respect to each other along a direction transverse to the z-axis. A detector module 114 includes a plurality of detector mosaics or tiles 116 arranged with respect to each other along the z-axis. In one instance, the detector array 112 is substantially similar to and/or based on the detector array described in U.S. Pat. No. 6,510,195B1, filed Jul. 18, 2001, and entitled "Solid State X-Radiation Detector Modules and Mosaics thereof, and an Imaging Method and Apparatus Employing the Same," which is incorporated herein by reference in its entirety.

Figure 2:
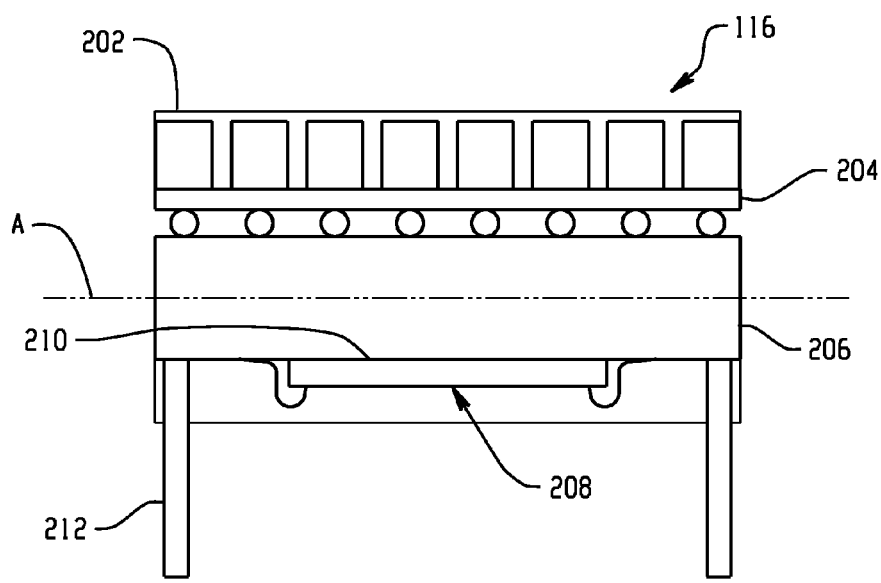
FIG. 2 illustrates an example detector tile.

Briefly turning to FIG. 2, a cross-sectional view of a tile 116 along line A-A of FIG. 1 is illustrated. The illustrated tile 116 includes a scintillator array 202 that is physically and optically coupled to a photosensor array 204, such as an array of back-illuminated photodiodes or other photosensitive pixels, which is coupled to a substrate 206. The photosensor array 204 can be bump-bonded (as shown) or otherwise coupled to the substrate 206. Electronics 208 are physically and electrically coupled to a read out area 210 of the substrate 206 electrically coupled to the photosensor array 204. The scintillator array 202, the photosensor array 204 and the electronics 208 are in substantial thermal communication. Electrical pathways 212 such as connector pins or other electrical pathways carry power supplies and digital I/O signals. An example of such a tile is described in "A New 2D-Tiled Detector For Multislice CT," Luhta et al., Medical Imaging 2006: Physics of Medical Imaging, Vol. 6142, pp. 275-286 (2006). Another suitable tile is described in international patent application serial number PCT/US2007/063532, filed on Mar. 8, 2007, and entitled "Radiation Detector Array," which is incorporated in its entirety by reference herein.

Figure 3:
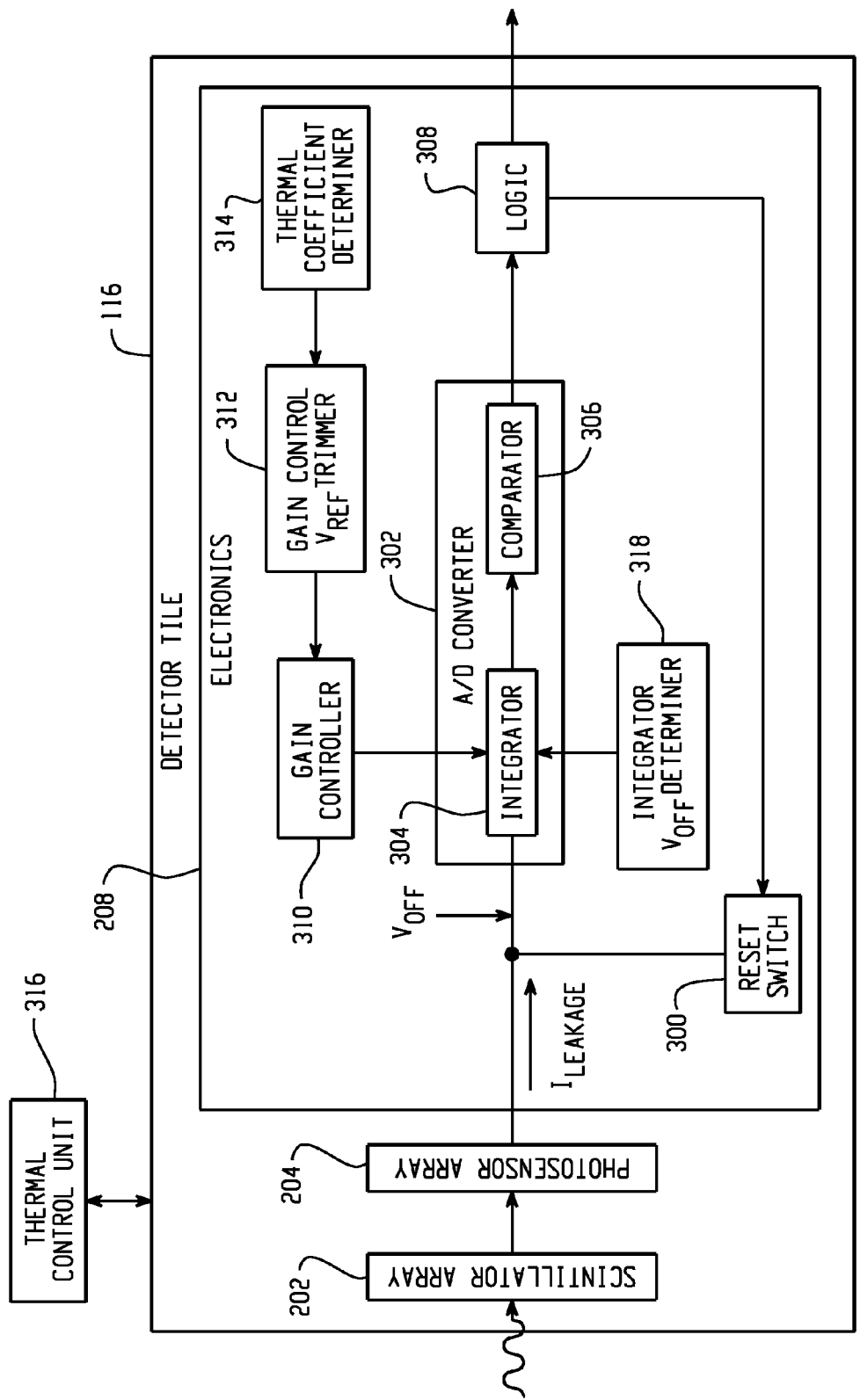
FIG. 3 illustrates example detector electronics.

FIG. 3 illustrates example electronics 208. An analog-to-digital (A/D) convertor 302 includes an integrator 304 and a comparator 306. The illustrated A/D converter 302 is configured as an electrical current-to-frequency (I/F) convertor that converts charge from the photosensor array 204 into a train of pulses having a frequency indicative of the charge. A logic unit 308 counts a number of pulses (C) from the comparator 306 during an integration period and determines a time from a first pulse to a last pulse (T) in the integration period. From this data, the logic unit 308 can determine the frequency (e.g., C/T), which is indicative of the input charge. A reset switch 300 resets the integrator 304 for each integration period. An example of such electronics is described in greater detail in U.S. Pat. No. 6,671,345B2, filed Nov. 7, 2001, and entitled "Data Acquisition for Computed Tomography," which is incorporated herein by reference in its entirety. Other suitable electronics are described in U.S. Pat. No. 4,052,620, filed Nov. 28, 1975, and entitled "Data Acquisition for Computed Tomography," which is also incorporated herein by reference in its entirety.

As described in greater detail below, in one embodiment the A/D converter 302 is configured to process both charge corresponding to impinging photons and residual charge from afterglow (dark current). In this embodiment, the source controller 110 pulses radiation emission during an integration period, as noted above, and the radiation signal is measured when radiation is being emitted and the dark current is measured when the radiation is off. With such an embodiment, the logic unit 308 is configured to process the output pulses from the comparator 306 for both the radiation signal and the dark current signal, and corrects or compensates the radiation signal based on the dark current signal. In one instance, this allows for use of scintillators with longer afterglow, which generally are less expensive than scintillators with shorter afterglow. As such, the above correction may facilitate reducing detector array 112 and/or overall system 100 cost.

A gain controller 310 sets the gain for the integrator 304, and a gain control voltage reference ($V_{REF}$) trimmer 312 generates a reference voltage for the gain controller 310. A thermal coefficient determiner 314 determines a reference voltage thermal coefficient for the electronics 208. As described in greater detail, this may include determining a reference voltage thermal coefficient based on the thermal coefficients of the scintillator array 202, the photosensor array 204, and/or other components. In one instance, this allows for less stringent (or no) thermal control of the detector array 112 relative to a configuration in which the thermal coefficient determiner 314 is omitted. Such thermal control is provided by a thermal control unit 316 that facilitates maintaining the temperature of the detector array 112 within a pre-determined temperature range during scanning. The thermal control unit 316 may include a heater, a fan, a heat sink, etc.

The illustrated electronics 208 further include an integrator voltage offset ($V_{OFF}$) determiner 318. The offset voltage is the voltage that appears at the integrator input and therefore on the photosensor array 204. This offset voltage in combination with the photosensor resistance causes leakage current in the photosensor. In one instance, the integrator $V_{OFF}$ determiner 318 provides a first offset voltage that reduces or substantially cancels photosensor array leakage current at the input of the integrator 304. In another instance, and as described in greater detail below, the integrator $V_{OFF}$ determiner 318 provides a second offset voltage that allows for measuring photosensor array leakage current and/or determining photosensor array resistance. This may allow for identifying mal or non-operating photosensor channels, and can be performed during photosensor, tile, and/or detector array 112 assembly, servicing, calibration, etc.

Returning to FIG. 1, a reconstructor 118 reconstructs the signal from the detector array 112 and generates volumetric image data indicative thereof. An image processor or the like can generate one or more images based on the image data. A general purpose computing system serves as an operator console 120. Software resident on the console 120 allows the operator to control the operation of the system 100 such as selecting a pulsed x-ray technique, placing the scanner in a scan mode or a photosensor array test mode, setting an electronics thermal coefficient, and/or other control. A patient support 122, such as a couch, supports an object or subject such as a human patient in the examination region 106.

Figure 4:
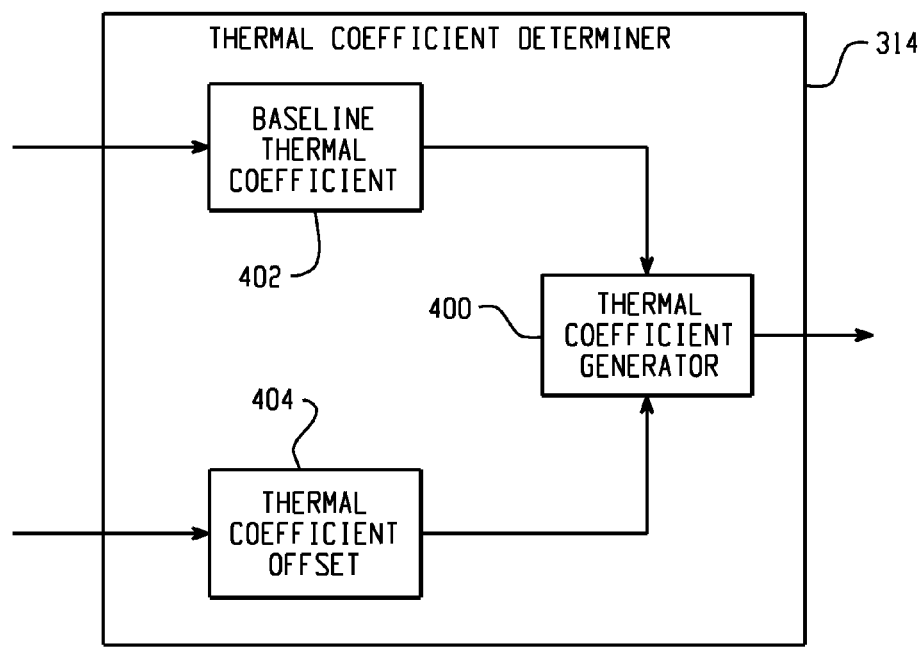
FIG. 4 illustrates an example thermal coefficient determiner.

FIG. 4 illustrates a non-limiting embodiment of the thermal coefficient determiner 314. In this example, a thermal coefficient generator 400 generates a thermal coefficient for the electronics 208 based on a baseline thermal coefficient 402 and a thermal coefficient offset 404. In one instance, the baseline thermal coefficient 402 is set to a predetermined value for the electronics 208, and the thermal coefficient offset 404 is set to be about equal to a negative of a summation of the scintillator array 202 and the photosensor array 204 thermal coefficients. The thermal coefficients of the scintillator array 202 and the photosensor array 204 can be measured, approximated, or otherwise determined. One or both of the thermal coefficients 402 and 404 can be stored in a storage element such as a register. In the illustrated example, the thermal coefficient generator 400 adds or sums the baseline thermal coefficient 402 and the thermal coefficient offset 404 to generate the thermal coefficient for the electronics.

By way of example, assume that the thermal coefficient for the scintillator array 202 is about −0.15%/C and that the thermal coefficient for photosensor array 204 is about +0.05%/C, and the aggregate thermal coefficient for the scintillator array 202 and the photosensor array 204 is about −0.10%/C. With this scenario, the thermal coefficient determiner 314 can be configured to provide a $V_{REF}$ thermal coefficient with a set point in a range between 0.0 to −0.20%/C such as about −0.10%/C±0.005%/C, which sets the thermal coefficient of the processing electronics at about +0.10%/C (Note that in the current-to-frequency converter the temperature coefficient of the overall A/D converter is the negative of the temperature coefficient of $V_{REF}$, which may reduce or substantially cancel the thermal coefficients of the scintillator array 202 and the photosensor array 204, rendering the thermal coefficient of the tile at about 0.00%/C. The above example is illustrated in Table 1.

TABLE 1

Example thermal coefficients

| | Thermal coefficient |
|---|---|
| scintillator array | ≈−0.15%/C. |
| photosensor array | ≈+0.05%/C. |
| processing electronics | ≈+0.10%/C. ($V_{REF}$ ≈ −0.10%/C.) |
| tile | ≈0.00%/C. |

Note that by reducing or substantially canceling the thermal coefficients of the scintillator array 202 and the photosensor array 204, the thermal control unit 316 (FIG. 3) can be omitted, or less stringent and less costly thermal control can be employed without compromising imaging performance. Further note that +0.10%/C corresponds to +1000 parts per million per degree Celsius (ppm/C).

In another embodiment, a register or other memory is programmed with a plurality of thermal coefficient offsets 404 (e.g., from 0.00%/C to +0.20%/C in increments of 0.01%/C or other increment). A flag or the like can be used to select the thermal coefficient offset to be used as the thermal coefficient offset 404. In another instance, the register is programmed with a plurality of scaling factors that scale the thermal coefficient offset 404. Likewise, a flag can be used to select the scaling factor to apply to the thermal coefficient offset 404. In yet another embodiment, the thermal coefficient offset 404 is omitted, and the baseline thermal coefficient 402 is set based on the scintillator array 202 and the photosensor array 204 thermal coefficients.

In still another instance, the baseline thermal coefficient 402 and/or the thermal coefficient offset 404 (if provided) can be otherwise determined and/or set. In the above example, the thermal coefficients of the scintillator array 202 and the photosensor array 204 are reduced or substantially cancelled via a bandgap reference voltage thermal coefficient. In another instance, the coefficients are reduced or substantially cancelled by setting the thermal coefficient of the electronics 208 externally through a detector bias adjuster, via circuitry common to a plurality of tiles 116, and/or otherwise.

In another non-limiting embodiment, the thermal coefficient determiner 314 and/or another component can identify a thermal coefficient mismatch between the photosensor array 204, the scintillator array 202 and the processing electronics 208 that exceeds a predetermined thermal coefficient mismatch threshold and changes the thermal coefficient of the processing electronics 208 so that the thermal coefficient of the processing electronics 208 is about equal to the negative of the summation of a thermal coefficient of the photosensor array 204 and the thermal coefficient of the scintillator array 202. Such a mismatch may occur over time. For example, the temperature coefficient of the scintillator array 202 and/or the photosensor array 204 may change over time due to radiation damage, long term exposure to radiation, and/or otherwise. As such, the temperature coefficient of the processing electronics can be subsequently adjusted to compensate for the temperature coefficient of the scintillator array 202 and/or the photosensor array 204. It is to be appreciated that this can be done as part of a calibration or other procedure.

Figure 5:
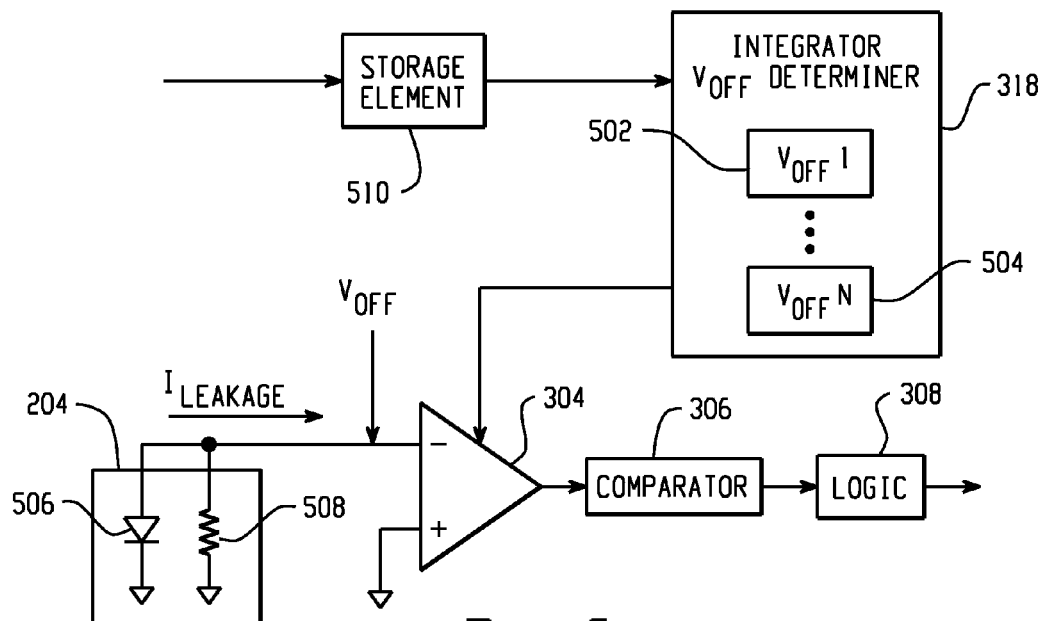
FIG. 5 illustrates an example voltage reference determiner

FIG. 5 illustrates a non-limiting embodiment of the integrator $V_{OFF}$ determiner 318. In this example, the photosensor array 204 is represented as a diode 506 and a resistor 508, with leakage current ($I_{Leakage}$) that adds to the input of the integrator 304. The illustrated integrator $V_{OFF}$ determiner 318 includes two or more offset voltages, offset voltage 1 ($V_{OFF}$ 1) 502, . . . , offset voltage N ($V_{OFF}$ N) 504, wherein N is an integer. In one instance, $V_{OFF}$ 1 502 is selected for scanning subjects or objects, and $V_{OFF}$ N 504 is selected for testing photosensors array 204 of a detector tile 116.

By way of example, in one embodiment a value of one of the reference voltages, for example, $V_{OFF}$ 1 502, corresponds to a value that substantially cancels or reduces $I_{Leakage}$. A value of another of the reference voltages, for example, $V_{OFF}$ N 504, corresponds to a voltage that induces a measurable current at the input of the integrator 304. For instance, $V_{OFF}$ N 504 can be determined based on an expected resistance of the resistor 508 and an electrical current that trips the comparator 306, as a function of the following equation: $V_{OFF\_N} = R_{expected\_resistance} * I_{measurable}$. In one example, $V_{OFF}$ N 504 is −1 to −50 mV (milliVolts) such as −10 mV so that the integrator input voltage is 1 to 50 mV higher than it would be if $V_{OFF}$ 1 502 was applied to the integrator input.

The above allows for computing the resistance of a photosensor based on $V_{OFF}$ N 504 and the measured current, and subsequently identifying photosensor channels with resistances outside of a predetermined range, which may facilitate identifying mal or non-operating photosensor channels during photosensor fabrication, detector array assembly, scanner calibration, scanner service, etc. A flag or the like in a storage element 510 such as a register or other memory indicates which reference voltage 502, . . . , 504 to use. The storage element 510 can be programmed with the references voltages 502, ..., 504 via authorized personnel such as a technician, an engineer, a user, and/or other authorized personnel.

Figure 6:
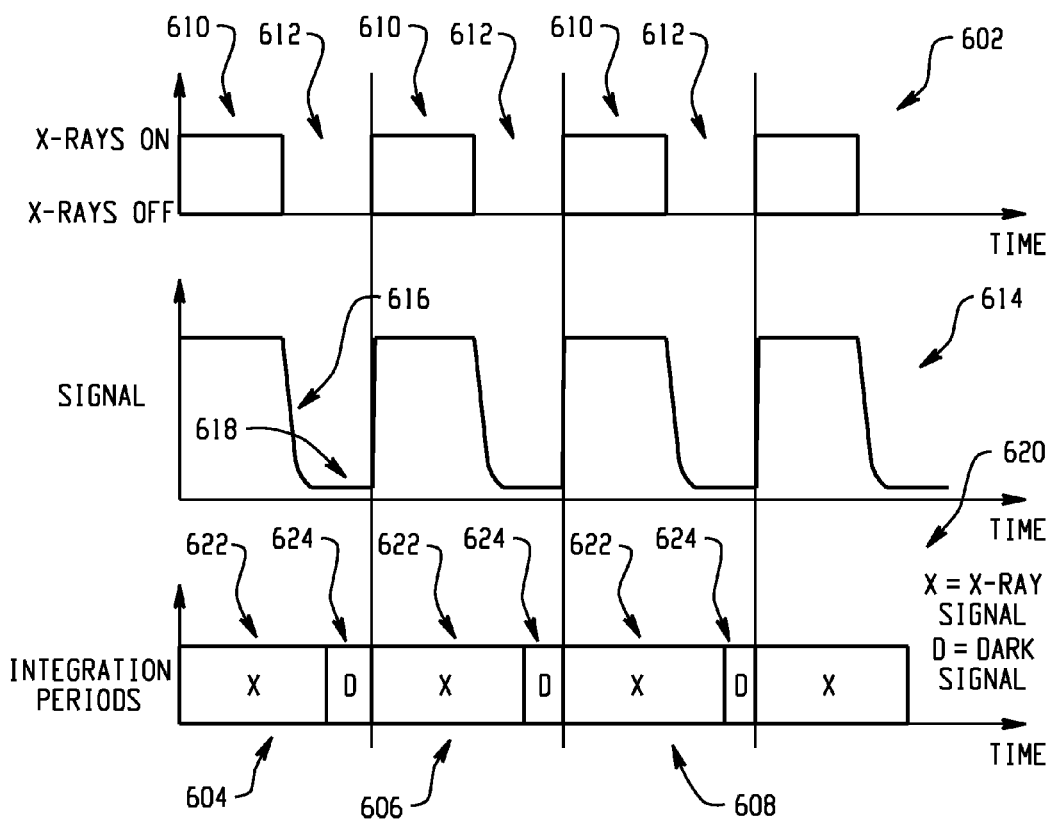
FIG. 6 illustrates example timing diagrams.

FIG. 6 shows suitable voltage source pulsing and data acquisition timing diagrams, and FIGS. 7, 8, 9 and 10 illustrate corresponding non-limiting embodiments of suitable A/D converter 302 and logic unit 308 configurations. As noted above, in one embodiment the radiation source controller 110 pulses the radiation source 108 to turn radiation on and off, the electronics 208 measures deposited charge when radiation is on and the dark current when radiation is off, and the logic unit 308 corrects the detected radiation signal based on the measured dark current.

Initially referring to FIG. 6, an example voltage source pulsing timing diagram 602 pulses the radiation source 108 with a duty cycle of about 55% per integration period 604, 606, 608. As such, radiation is turned on during a first sub-portion 610 of the integration periods 604-608 and off during a second sub-portion 612 of the integration periods 604-608. This illustrated duty cycle is provided for explanatory purposes and is not limiting. For example, in another embodiment the duty cycle can be greater than 55% such as 90%, 95% and 99%. The duty cycle may also be less then 55%. Furthermore, the radiation source 108 may not be pulsed in every integration period and/or the duty cycle may vary between integration periods.

A photosensor array output curve 614 shows example corresponding photosensor output current. As noted above, the charge deposited on the scintillator array 202 decays with a long time constant (afterglow). As a consequence, the output of the photosensor array 204, when radiation is off, abruptly decreases as shown at 616 and then levels to some smaller value that falls off with the long charge decay constant of the scintillator array 202 as shown at 618. A data acquisition timing diagram 620 shows that the electronics 208 can be employed to process the signal corresponding to the deposited charge (X) when radiation is on until after the abrupt signal decrease as shown at 622 and to process the dark current signal (D) once the decaying charge settles and falls off more slowly as shown at 624.

Figure 7:
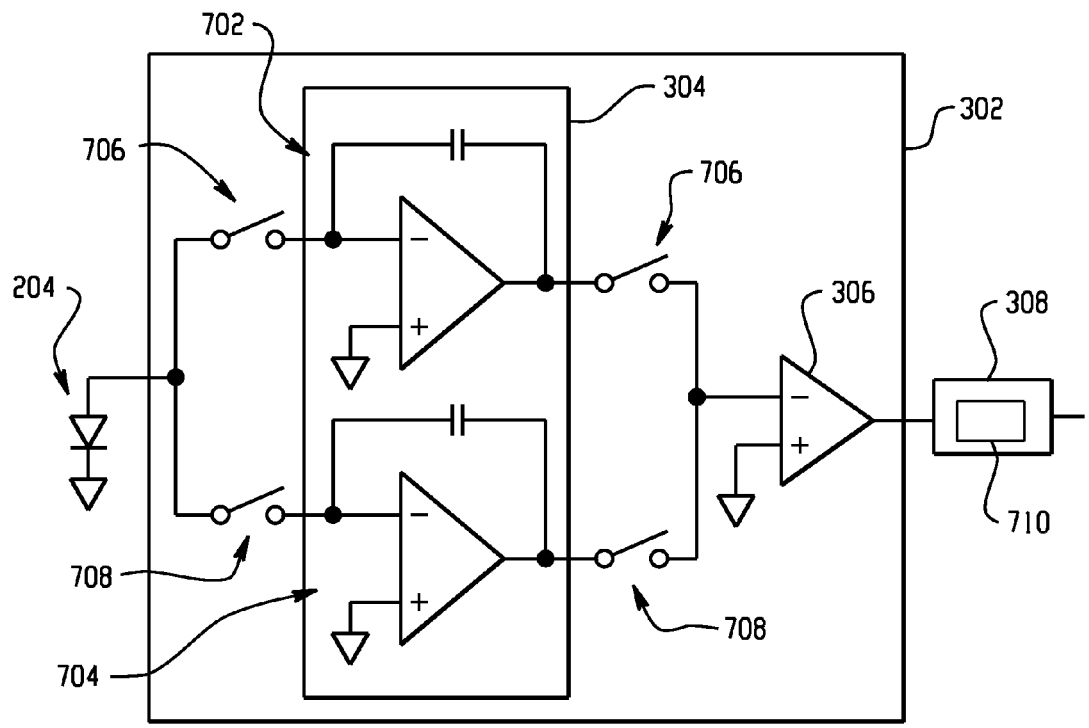
FIGS. 7-10 illustrate example A/D converters and logic.

FIG. 7 illustrates a non-limiting embodiment of the A/D converter 302 and the logic unit 308. In this embodiment, the integrator 304 includes two channels or sub-integrators, including a first integrator 702 for processing the charge signal and a second integrator 704 for processing the dark current. First and second switches 706 and 708 alternately open and close to route the signal from the photosensor array 204 respectively to the first and second sub-integrators 702 and 704. In one instance, the logic unit 308 controls the switches 706 and 708 based on the timing diagrams of FIG. 6 or otherwise. The comparator 306 processes the signal from the integrators 702 and 704, and the logic unit 308 processes the signal from the comparator 306. The logic unit 308 includes a corrector 710 that corrects the charge signal based on the dark current signal or an average of the dark current signal over two or more integration periods. In this example, the corrector 710 subtracts the dark current from the charge signal.

Figure 8:
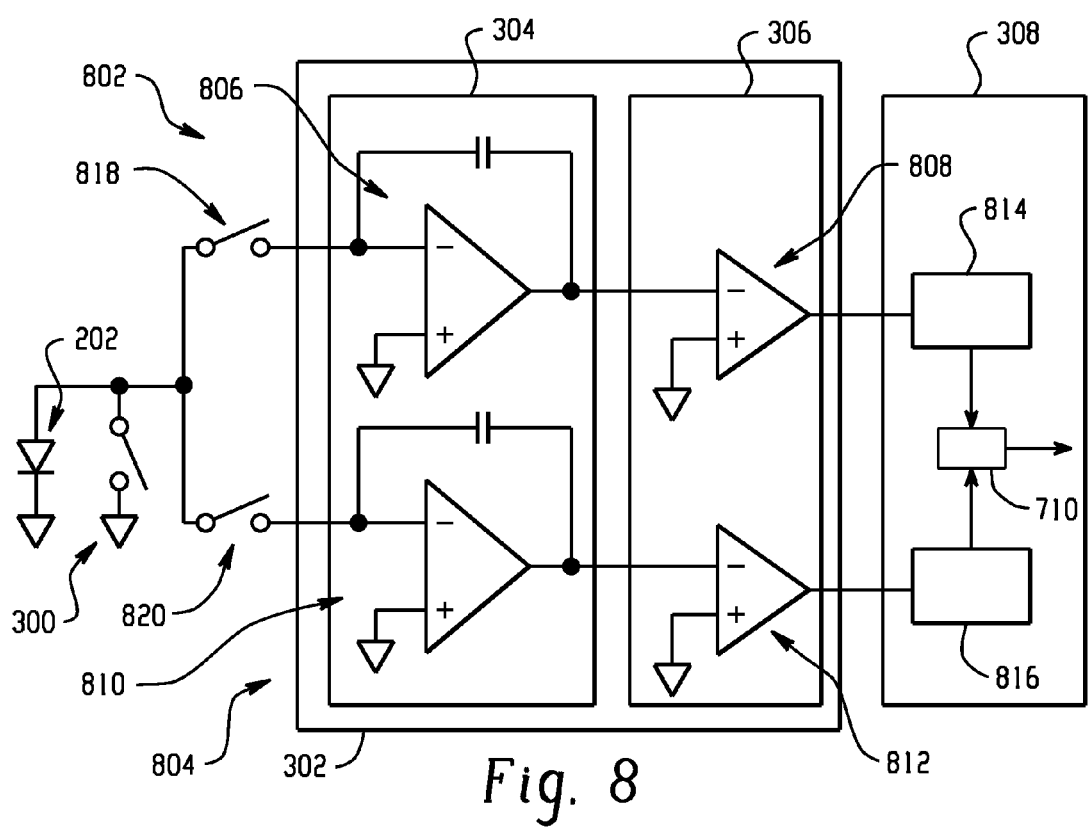

FIG. 8 illustrates another non-limiting embodiment of the A/D converter 302 and the logic unit 308. In this embodiment, the A/D converter 302 includes two processing channels, including a first channel 802 for processing the charge signal and a second channel 804 for processing the dark current. The first channel 802 includes a first integrator 806 and a first comparator 808, and the second channel 804 includes a second integrator 810 and a second comparator 812. The logic unit 308 includes two sub-units, including a first sub-unit 814 for processing the output of the first channel 802 and a second sub-unit 816 for processing the output of the second channel 804, and the corrector 710. First and second switches 818 and 820 respectively open and close the channels 802 and 804. Similar to FIG. 8, the logic unit 308 alternately toggles the switches 818 and 820 based on the timing diagrams of FIG. 6 or otherwise. The logic unit 308 activates the reset switch 300 to reset the A/D converter 302 on integration period boundaries, and, in some instance, when toggling the switches 818 and 820. Again, the corrector 710 subtracts the dark current from the charge signal.

Figure 9:
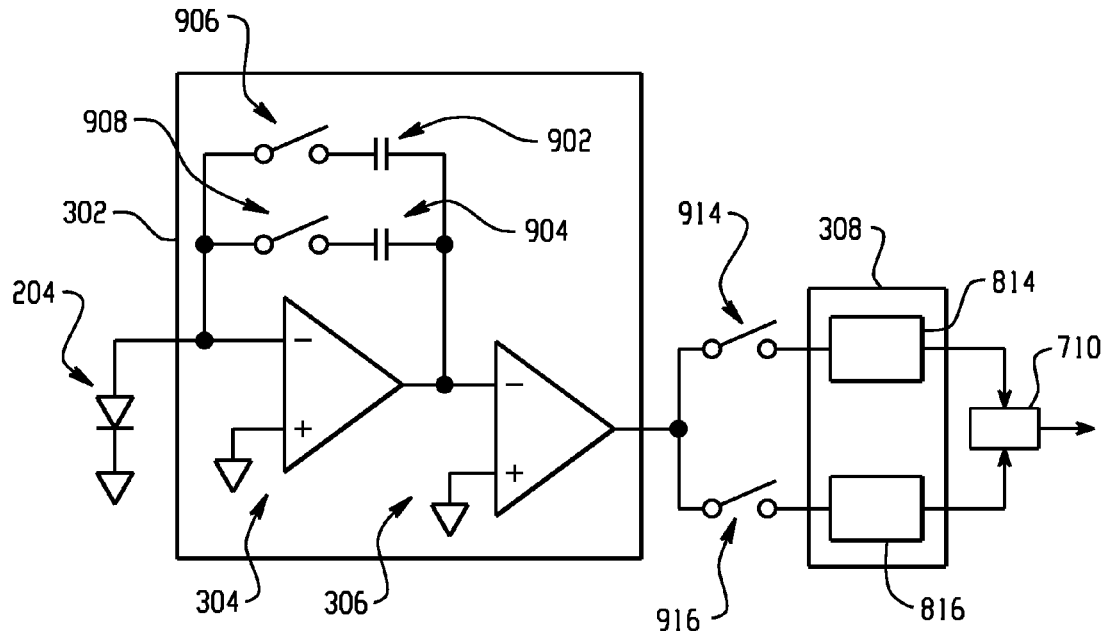

FIG. 9 illustrates another non-limiting embodiment of the A/D converter 302 and the logic unit 308. In this embodiment, the integrator 304 includes first and second integrating capacitors 902 and 904 configured in a parallel arrangement. A first switch 906 is in series with the first integrating capacitor 902, and a second switch 908 is in series with the second integrating capacitor 904. The logic unit 308 includes first and second logic sub-units 814 and 816. A third switch 914 is in series with the first sub-unit 814 of the logic unit 308, and a fourth switch 916 is in series with the second sub-unit 816 of the logic unit 308. In this example, the first integrating capacitor 902 and the first sub-unit 814 process the charge signal, and the second integrating capacitor 904 and the second sub-unit 816 process the dark current signal. The logic unit 308 can control the switches 906 and 914 and 908 and 916 based on the timing diagrams of FIG. 6 or otherwise. The corrector 710 subtracts the dark current from the charge signal.

Figure 10:
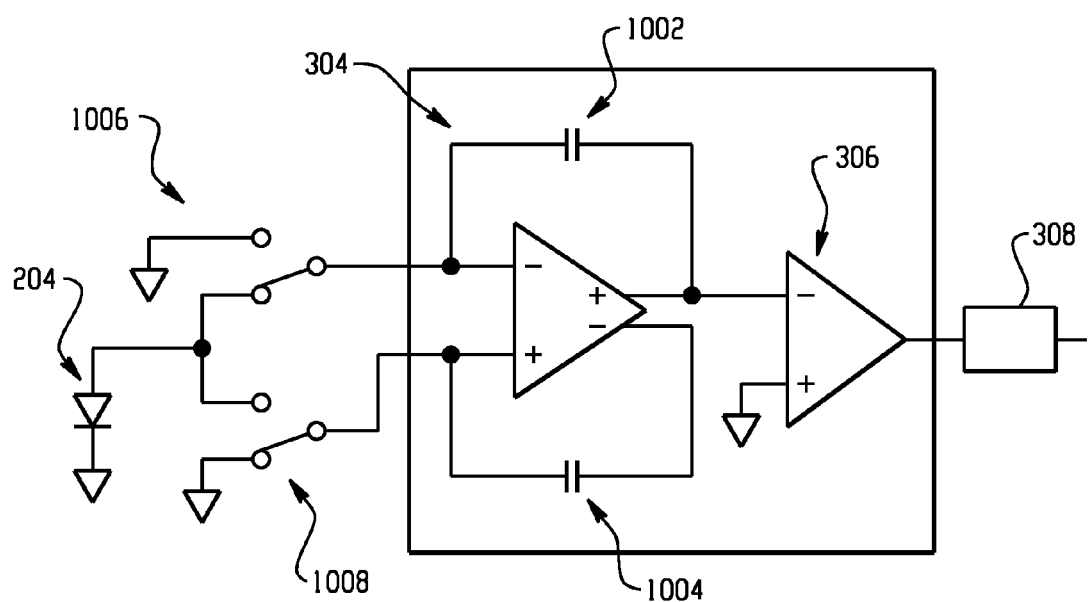

FIG. 10 illustrates another non-limiting embodiment of the A/D converter 302. The illustrated integrator 304 includes first and second integrating capacitors 1002 and 1004. A value of the first integrating capacitor 1002 is greater than a value of the second integrating capacitor 1004 by a known factor X. For example, the value of the first integrating capacitor 1002 may be 2, 4, 8, 16, 32, etc. times greater then the value of the second integrating capacitor 1004. The logic unit 308 alternately opens and closes the first and second switches 1006 and 1008 based on the acquisition timing diagrams of FIG. 6. When the charge signal is being integrated, the first integrating capacitor 1002 discharges as usual. When the dark current signal is being integrated, the first integrating capacitor 1002 charges faster than the second integrating capacitor 1004 by the known factor X. This allows for subtraction of the dark current signal in the analog domain.

It is to be appreciated that the embodiments described herein and variations thereof can also be employed in connection with a smart detector, such as the smart detector described in connection with U.S. patent application Ser. No. 12/159,861, filed on Jan. 4, 2007, and entitled "Smart Radiation Detector Module," which is incorporated in its entirety by reference herein. In one instance, this allows for automation and/or dynamic control of various functionality such identifying thermal coefficient mismatch between the photosensor array 204, the scintillator array 202 and the processing electronics 208 that exceeds a predetermined thermal coefficient mismatch threshold and mitigating the mismatch and/or other functionality.

Figure 11:
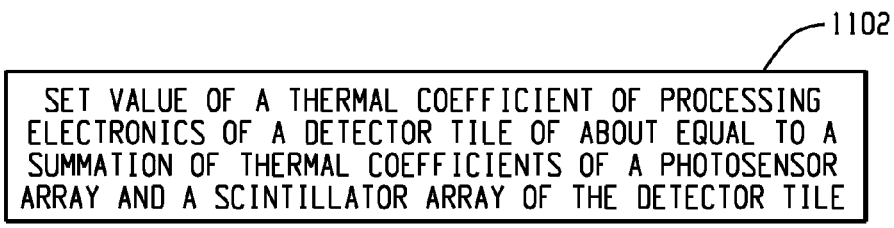
FIGS. 11-13 illustrate example A/D converters and logic.

FIG. 11 illustrates a method for adjusting a detector thermal coefficient. At 1102, a value of a thermal coefficient of processing electronics of a detector tile of an imaging system is set about equal to a summation of thermal coefficients of a photosensor array and a scintillator array of the detector tile.

Figure 12:
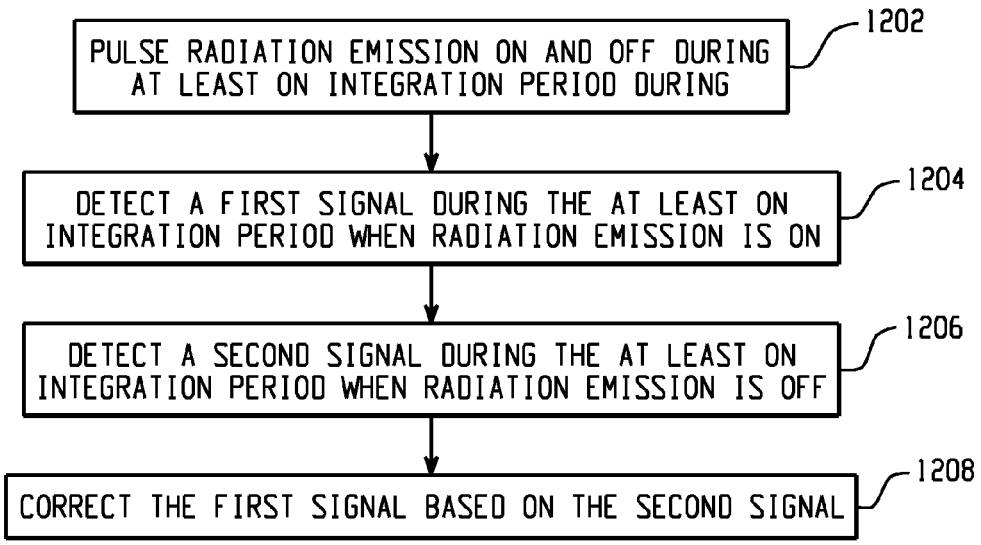

FIG. 12 illustrates a method for correcting detected radiation for dark current. At 1202, radiation emission is pulsed on and off during at least on integration period during an imaging procedure. At 1204, a first signal is detected during the at least one integration period when radiation emission is on. At 1206, a second signal is detected during the at least one integration period only when radiation emission is off. At 1208, the first signal is corrected based on the second signal.

Figure 13:
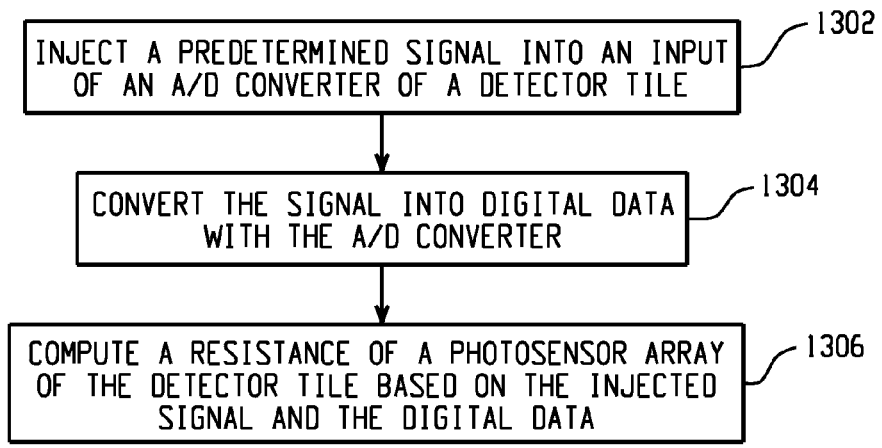

FIG. 13 illustrates a method for correcting detected radiation for dark current. At 1302, a predetermined signal is injected into an input of an A/D converter of a detector tile. The signal is measurable by the A/D converter. At 1304, the signal is converted into digital data with the A/D converter. At 1306, a resistance of a photosensor array of the detector tile is computed based on the injected signal and the digital data.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. An imaging detector, comprising:
   a photosensor array having a light sensitive side and an opposing read out side;
   a scintillator array optically coupled to the light sensitive side of the photosensor array; and
   processing electronics electrically coupled to the read out side of the photosensor array, wherein the photosensor array, the scintillator array and the processing electronics are in thermal communication, and a value of a thermal coefficient of the processing electronics is about equal to a negative of a summation of a thermal coefficient of the photosensor array and a thermal coefficient of the scintillator array.

2. The detector of claim 1, wherein the processing electronics includes a current-to-frequency converter that converts charge output of the photosensor array into digital data with a frequency indicative of the charge output.

3. The detector of claim 1, wherein the value of the thermal coefficient of the processing electronics substantially cancels the thermal coefficient of the photosensor array and the thermal coefficient of the scintillator array.

4. The detector of claim 1, wherein a net thermal coefficient of the processing electronics, the photosensor array and the thermal coefficient of the scintillator array is about 0.00%/Celsius.

5. The detector of claim 1, further comprising:
   a thermal coefficient determiner that determines the thermal coefficient of the processing electronics based on the thermal coefficients of the photosensor array and the scintillator array.

6. The detector of claim 5, wherein the thermal coefficient determiner identifies a thermal coefficient mismatch between the photosensor array, the scintillator array and the processing electronics that exceeds a predetermined mismatch threshold and changes the thermal coefficient of the processing electronics so that the thermal coefficient of the processing electronics is about equal to the negative of the summation of a thermal coefficient of the photosensor array and the thermal coefficient of the scintillator array.

7. The detector of claim 1 wherein the thermal coefficient of the processing electronics is programmable.

8. The detector of claim 1, the processing electronics comprising:
   an A/D converter that alternately converts a first charge signal corresponding to impinging radiation into a first digital signal and a second charge signal corresponding to decaying scintillator charge into a second digital signal; and
   a logic unit that corrects the first digital signal based on the second digital signal.

9. The detector of claim 1, the processing electronics further comprising:
   an A/D converter that converts the output of the photosensor array into a digital signal;
   an integrator offset voltage signal determiner that provides an integrator offset voltage signal to the A/D converter that induces an electrical current measurable by the A/D converter, and
   a logic unit, wherein the A/D converter measures the induced electrical current and the logic unit computes a resistance of the photosensor array based on the integrator reference voltage signal and the measured electrical current.

10. An imaging system, comprising:
    a radiation source that generates a radiation beam that traverses an examination region;
    a source controller that pulses the radiation source;
    a detector array that detects radiation that traverses the examination region;
    a reconstructor that reconstructs that output of the detector array and generates imaged data indicative thereof;
    wherein the detector array includes a plurality of detector tiles, a detector tile, comprising:
    a photosensor array;
    a scintillator array optically coupled to the photosensor array; and
    processing electronics electrically coupled to the photosensor array, wherein the photosensor array, the scintillator array and the processing electronics are in thermal communication, and a value of a thermal coefficient of the processing electronics substantially cancels thermal coefficient of the photosensor array and the scintillator array.

11. The imaging system of claim 10, the processing electronics, comprising:
    an A/D converter that converts charge output by the photosensor array into a digital signal having a frequency indicative of the charge, wherein the A/D converter alternately converts first charge corresponding to impinging radiation into a first signal and second charge corresponding to decaying charge into a second signal; and
    a logic unit that corrects the first signal based on the second signal.

12. The imaging system of claim 10, the processing electronics, comprising:
    an A/D converter converts charge output by the photosensor array into a digital signal having a frequency indicative of the charge; and
    an integrator voltage offset signal determiner that generates an integrator offset voltage signal for the A/D converter that induces an electrical current measurable by the A/D converter,
    wherein the A/D converter measures the induced electrical current and the logic unit computes a resistance of the photosensor array based on the integrator reference voltage signal and the measured electrical current.

13. A method, comprising:
    setting a value of a thermal coefficient of processing electronics of a detector tile of an imaging system about equal to a summation of thermal coefficients of a photosensor array and a scintillator array of the detector tile.

14. The method of claim 13, wherein the processing electronics includes an A/D converter that converts charge output by the photosensor array into a digital signal having a frequency indicative of the charge.

15. The method of claim 13, wherein the value of the thermal coefficient of processing electronics is programmable.

\* \* \* \* \*